United States Patent

Pipino

[11] Patent Number: 5,986,768
[45] Date of Patent: Nov. 16, 1999

[54] INTRA-CAVITY TOTAL REFLECTION FOR HIGH SENSITIVITY MEASUREMENT OF OPTICAL PROPERTIES

[75] Inventor: Andrew Charles Rule Pipino, Gaithersburg, Md.

[73] Assignee: The United States of America, as represented by the Secretary of Commerce, Washington, D.C.

[21] Appl. No.: 09/188,415

[22] Filed: Nov. 10, 1998

Related U.S. Application Data

[63] Continuation-in-part of application No. 08/962,170, Oct. 31, 1997, and a continuation-in-part of application No. 08/962,171, Oct. 31, 1997, Pat. No. 5,835,231.

[51] Int. Cl.⁶ .................................................. G01N 21/00
[52] U.S. Cl. ........................ 356/440; 356/136; 356/244; 356/445
[58] Field of Search .................................. 356/439, 440, 356/246, 445, 432, 136, 244

[56] References Cited

U.S. PATENT DOCUMENTS

| | | | |
|---|---|---|---|
| 4,571,085 | 2/1986 | Anderson | 356/445 |
| 4,793,709 | 12/1988 | Jabr et al. | 356/445 |
| 5,437,840 | 8/1995 | King et al. | 356/346 X |
| 5,528,040 | 6/1996 | Lehmann | 356/439 |

Primary Examiner—Robert H. Kim
Attorney, Agent, or Firm—Larson and Taylor

[57] ABSTRACT

An optical cavity resonator device is provided for conducting sensitive measurement of optical absorption by matter in any state with diffraction-limited spatial resolution through utilization of total internal reflection within a high-Q (high quality, low loss) optical cavity. Intracavity total reflection generates an evanescent wave that decays exponentially in space at a point external to the cavity, thereby providing a localized region where absorbing materials can be sensitively probed through alteration of the Q-factor of the otherwise isolated cavity. When a laser pulse is injected into the cavity and passes through the evanescent state, an amplitude loss resulting from absorption is incurred that reduces the lifetime of the pulse in the cavity. By monitoring the decay of the injected pulse, the absorption coefficient of manner within the evanescent wave region is accurately obtained from the decay time measurement.

9 Claims, 1 Drawing Sheet

5,986,768

INTRA-CAVITY TOTAL REFLECTION FOR HIGH SENSITIVITY MEASUREMENT OF OPTICAL PROPERTIES

This application is a continuation-in-part of copending U.S. application Ser. No. 08/962,170, filed Oct. 31, 1997, and U.S. application Ser. No. 08/962,171, filed Oct. 31, 1997, now U.S. Pat. No. 5,835,231, the disclosures of which are hereby incorporated by reference.

BACKGROUND OF THE INVENTION

1. Field of the Invention

The present invention relates to matter identifying devices, and more particularly, to those that measure the optical absorption by matter within an evanescent wave field generated by total internal reflection within a low-loss optical cavity.

2. Related Art

Optical absorption spectroscopy is fundamentally important in chemical analysis, providing decisive quantitative and qualitative information. Such diagnostic capabilities find substantial utility in both research and industrial process environments. Therefore, an advancement in sensitivity, accuracy, or adaptability of the technique will have a significant impact.

Absorption is usually determined from measurement of a ratio of optical powers at a certain wavelength. Recently, a new technique, termed cavity ring-down spectroscopy (E. K. Wilson, *C&E News*, Feb. 19, 1996, p. 34, incorporated herein by reference), has been developed to determine absorption by gases, which utilizes a pulsed light source and an optical cavity. Typically, a light pulse from a laser source is injected into a cavity which is formed by two high-reflectivity mirrors. The lifetime of the pulse in the cavity is highly sensitive to cavity losses, including absorption by gases. Measurement of the pulse decay time or "ring-down" time in the cavity can thereby provide a direct measure of absorption. Cavity ring-down eliminates the adverse effects of light source fluctuation, since the measurement is acquired with a single pulse of light. The feasibility of this technique arises from recent technological advances in optical polishing, which permit the fabrication of extremely low-scatter-loss optics. If ordinary optics such as high-reflectivity mirrors (R~99%)are used, the pulse lifetime in the cavity is too short for the cavity ring-down strategy to provide a significant improvement in sensitivity, as compared to conventional absorption methods. However, with the advent of superpolishing, such as that described in N. J. Brown, *Ann. Rev. Mater. Sci.* 16, p. 371 (1986), incorporated herein by reference, mirrors with 99.99% reflectivity or better can be fabricated to construct low-loss optical cavities, thereby permitting ultra-high sensitivity to be routinely realized. The cavity ring-down technique has thereby become a viable form of optical absorption metrology, with trace analysis capabilities that greatly exceed conventional absorption methods.

A stable optical cavity used to measure the optical absorption of a material, as disclosed in copending application Ser. No. 08/962,170, is shown in FIG. 1. A three element cavity 5 is formed by two high-reflectivity concave mirrors 10, 12 with equal radii of curvature, and a Pellin-Broca prism 14 in a right-angle configuration. A light source 15 for injecting light, described throughout as a laser, is positioned adjacent mirror 10, and a photomultiplier 19 is positioned adjacent mirror 12. The Pellin-Broca prism 14 provides a total internal reflection with very high internal transmission for a light beam 16a that is polarized in the plane formed by the three element cavity 5, since an incident beam 16b and an exiting beam 16c traverse the prism faces at the Brewster's angle $N_B$. By properly mounting the Pellin-Broca prism 14, the light beam will traverse the Pellin-Broca prism 14 at minimum deviation, which minimizes aberrations and beam translation with rotation about Brewster's angle $N_B$. Since the total internal reflection occurs at a hypotenuse surface 14a of the Pellin-Broca prism 14, an evanescent wave 18 decays exponentially into the region external to the hypotenuse surface 14a. Absorbing materials (not shown) placed within the decay length of the evanescent wave 18 can thereby be sensitively probed through the change in the decay time of a laser pulse injected into cavity 5. This decay time is detected by photomultiplier 19 which senses a very small portion of the injected light which escapes through mirror or reflector 12. Cavity losses for the configuration shown in FIG. 1 are largely determined by surface roughness induced scattering, although stress-birefringence of the Pellin-Broca prism 14 may induce polarization scrambling.

The optical cavity shown in FIG. 1 includes high-reflectivity concave mirrors 10 and 12 located a distance from the prism 14. The mirrors 10 and 12 must be properly aligned with each other and the prism 14 in order for the cavity to operate properly.

SUMMARY OF THE INVENTION

In accordance with the invention, a device is provided which permits the sensitive measurement of optical absorption by matter in any state with diffraction-limited spatial resolution through utilization of total internal reflection within a high-Q (high-quality, low-loss) optical cavity. The optical cavity consists of a single optical element. The use of a single optical element for the cavity eliminates the requirement of properly aligning the elements found in related optical cavities and results in a more rugged structure. Intra-cavity total reflection generates an evanescent wave that decays exponentially in space at a point external to the cavity, thereby providing a localized region where absorbing materials can be sensitively probed through alteration of the Q-factor of the otherwise-isolated cavity. When a light pulse is injected into the cavity and passes through the evanescent state, an amplitude loss resulting from absorption is incurred that reduces the lifetime of the pulse in the cavity. By monitoring the decay of the injected pulse, the absorption coefficient of matter within the evanescent wave region, is accurately obtained from the decay time measurement. In some embodiments of the invention, microsampling with high-spatial resolution is achieved through repeated refocussing of the light pulse at the sampling point, under diffraction-limited conditions.

In accordance with a first embodiment of the invention, an intra-cavity total reflection apparatus for high sensitivity measurement of the optical absorption of a test material is provided which comprises: an injecting means for producing light for a predetermined length of time; an optical cavity, comprising first, second and third reflecting surfaces integrally formed on a cavity medium, for receiving the light produced by the injecting means and for providing total internal reflection of the light within the cavity so as to generate an evanescent wave at the third reflecting surface which decays within a decay length outside of the cavity beyond the third reflecting surface, the test material being disposed outside of the cavity within the decay length, and the injected light oscillating between the first and second reflecting surfaces such that a portion of the injected light escapes from the cavity; and a measuring means disposed adjacent one of the first and the second reflecting surfaces for monitoring the portion of the injected light that escapes from the cavity to determine the amount of decay time the light takes to decay within the cavity.

Advantageously, the measuring means comprises a photomultiplier.

In one preferred implementation of this embodiment, the first and the second reflecting surfaces are orthogonal to one another.

The cavity medium is preferably formed of fused silica.

In another preferred implementation of this embodiment, the injecting means and the measuring means are optically coupled to the optical cavity with fiber-optic waveguides.

It is preferred that the third reflecting surface is a convex surface.

The injecting means preferably comprises a laser and more preferably comprises one of a pulsed dye laser, a picosecond pulsed laser, a femtosecond pulsed laser and a continuous wave laser. In another preferred embodiment, the laser comprises a diode laser.

Other features and advantages of the invention will be set forth in, or apparent from, the following detailed description of the preferred embodiments of the invention.

DETAILED DESCRIPTION OF THE PREFERRED EMBODIMENTS

Figure 1:
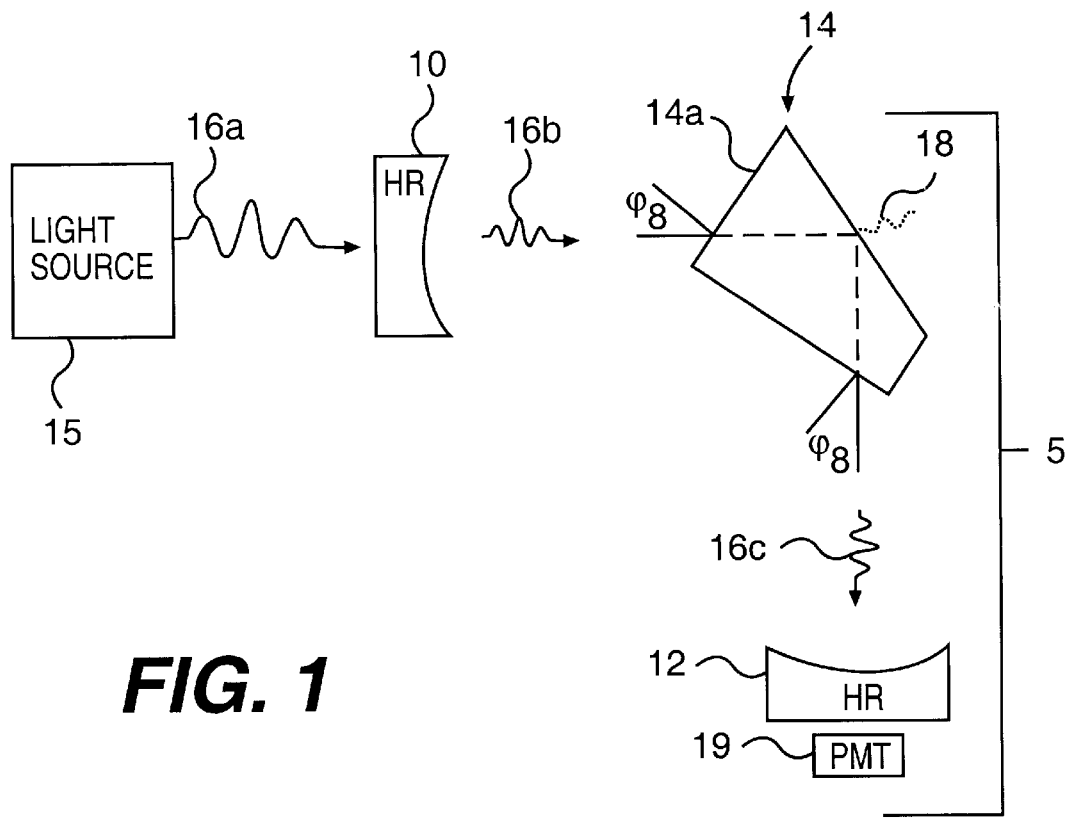
FIG. 1 is a schematic top elevational view of a multiple element optical cavity.

A further preliminary discussion is thought to be helpful at this point in fully understanding the invention. The measurement of optical absorption is fundamental to science and engineering, since an absorption spectrum provides a fingerprint which permits the qualitative and quantitative analysis of material composition. Absorption measurements are also frequently used to extract rates of chemical reactions and other processes. Key objectives in the development of a new technology for measurement of absorption are: 1) a reduction of the minimum detectable described in N. J. Brown, *Ann. Rev. Mater. Sci.* 16, p. 371 (1986), incorporated herein by concentration, 2) an increase in the spatial resolution of the measurement, and 3) the incorporation of tunable, powerful, and highly monochromatic laser sources. By reducing the detection limit, important chemical reactions and processes that involve trace quantities or very short path lengths will be, in some cases, detectable for the first time or examined with higher signal-to-noise ratio thereby allowing more reliable quantification.

Previous attempts to increase the limit of detection have typically increased the sampled path length, which inherently results in a decrease in spatial resolution. A few devices have been developed which permit multiple sampling of a specific region, but typically with a small number of passes and a large beam diameter. The device of the present invention which uses a multiple-pass geometry with refocussing, substantially improves sensitivity and spatial resolution. Furthermore, by using a laser source with the device of the invention, the spatially coherent nature of laser light permits greater spatial resolution, since a focal spot size limited only by diffraction can be readily achieved. The laser-based device also benefits from the high output power and broad wavelength range obtainable through the combination of tunable, pulsed dye lasers and harmonic generation. Considering the current technological trend toward the micro- and nanostructured domains, the development of a sensitive absorption device with high-spatial resolution will likely facilitate technological innovations. However, to obtain the advantages of a pulsed laser source, the device circumvents the complication of pulse-to-pulse fluctuation, which is characteristic of pulsed laser systems. These measurements of optical absorption by intra-cavity total reflection achieve high-sensitivity with high-spatial resolution.

In the case of Attenuated Total Reflection (ATR) developed extensively by Harrick, *Internal Reflection Spectroscopy*, by N. J. Harrick (Interscience Publishers, New York 1967), incorporated herein by reference, an evanescent wave is generated by internal reflection in an optical cavity such as a prism, plate or thin-film waveguide at an internal angle of incidence that exceeds the critical angle. In ATR spectroscopy, the evanescent wave generated by total internal reflection at the base of a prism is used for optical absorption measurements by the conventional optical power ratio method. Absorption is determined from the optical power loss incurred in the critically reflected beam relative to total reflection when no absorbing material is present in the evanescent wave region.

ATR can be used to measure absorption for samples in the solid, liquid or gas phases, but is also highly effective for probing powders, fibers, thin-films, and absorbed molecular monolayers. For studies of thin-films and monolayers, ATR benefits from the enhanced surface electric field which exists at the interface where total reflection occurs. The direction of the surface field can also be controlled through polarization selection to probe molecular orientation effects, which can be important in, for example, catalysis and adhesion.

In optical cavity ATR, a light beam is coupled into a mode of an optical cavity, which contains an evanescent wave component that decays exponentially outside of the waveguide. Absorbing material within the decay length is then probed by measuring a corresponding power loss in the out-coupled beam after traversing the waveguide for a predetermined distance.

Waveguide cavity ATR has the advantage over ordinary ATR of increased effective path length, since light rays coupled into the cavity experience a large number of internal reflections over a short distance. The effective path length is proportional to the product of the total number of reflections and the evanescent wave decay length. However, conventional waveguide cavity ATR still employs an optical power ratio measurement, which ultimately limits its utility in trace analysis.

Although optical cavities have been described in many patents and publications, this does not detract from the originality of novel applications of such technology. For example, laser resonators and spectrum analyzers are common implementations of optical cavities, which in some cases use identical cavity designs.

The sensitivity of the measurement can be increased by utilizing optical element geometries that permit multiple total internal reflections and/or multiple passes to occur. Multiple reflections increase sensitivity with a concomitant decrease in spatial resolution by sampling at multiple points to yield an increase in the effective path length. A multiple-pass strategy repeatedly samples a single region to provide moderate spatial resolution. However, multiple pass elements typically provide only a few passes and do not refocus the beam at the sampled region to increase spatial resolution.

Therefore, the development of an absorption technique which incorporates the powerful diagnostic capabilities of ATR and multiple-pass sampling with diffraction limited refocussing would represent a fundamental advancement in absorption measurement technology.

Apart from ATR is the cavity ring-down spectroscopy (CRDS) technique described in A. O'Keefe and D. A. G. Deacon, *Rev. Sci. Instrum.* 59, p. 2544 (1988) incorporated herein by reference, which is used for measuring the optical absorption spectra of gases. This technique was originally applied to narrowband gas phase absorption spectroscopy. U.S. Pat. No. 5,313,270 to Fishman and Haar, incorporated herein by reference, describes essentially identical technology to that of the O'Keefe reference mentioned above, with an intended application to the measurement of mirror reflectivity.

In CRDS, a single laser pulse is injected into a high-Q optical cavity, typically comprising a pair of concave high-reflectivity mirrors. Since the cavity Q-factor is high, the pulse makes many round trips, incurring only a small loss in amplitude per pass due to small intrinsic cavity losses resulting from, for example, mirror surface roughness scattering. Typically, the cavity is enclosed in a chamber which is filled with a gas of interest. When the frequency of the injected pulse corresponds to a resonant transition of the gas, the pulse amplitude loss per pass directly reflects the magnitude of the absorption. The temporal decay of the injected pulse is determined by monitoring the weak transmission which escapes from the cavity through one of the high-reflectivity mirrors. The transmitted intensity decays exponentially at a rate which reflects the total cavity losses, including absorption losses. Measurement of absorption is thereby achieved through a measurement of decay time instead of through a ratio of optical intensities. This time based measurement is equivalent to a large number of power ratio measurements with the same laser pulse, which inherently improves the accuracy and precision of the measurement since use of a single pulse eliminates the adverse effects of pulse-to-pulse fluctuation.

CRDS has only been applied to gas phase measurements, since the use of condensed matter sampling schemes which are common to transmission measurements, result in substantial intrinsic cavity losses which degrade the system performance. However, by utilizing intra-cavity total reflection, the advantages of a time-based absorption measurement can be combined with the advantages of ATR. The net result is a novel strategy for measurement of optical absorption by all states of matter. This strategy is fundamentally different from ATR, since a measurement of time instead of a ratio of intensities, is utilized. This strategy is different from CRDS since condensed matter can be probed through generation of an evanescent wave. Furthermore, the highly-localized nature of the evanescent wave combined with the spatial coherence provided by a laser source permits diffraction-limited spatial resolution and provides a decisively defined sample path length, which is necessary for accurate quantitative measurements.

Figure 2:
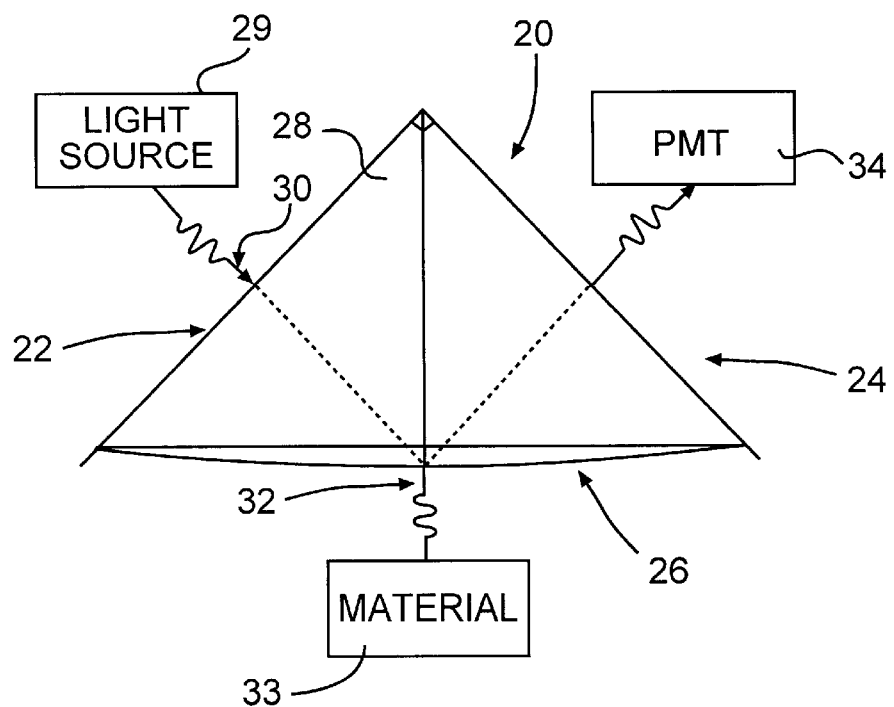
FIG. 2 is a schematic top elevational view of a single optical element optical cavity in accordance with a preferred embodiment of the invention.

Turning now to the embodiment shown in the FIG. 2, this embodiment takes advantage of the strategy discussed in the preceding paragraph, and the illustrated device is an intra-cavity total reflection device comprising a high-Q optical cavity. Losses introduced by any element in the system must be extremely small to produce a high-Q cavity.

It is noted that the preferred embodiment illustrated in FIG. 2 uses narrowband, multilayer coatings or Brewster's angle to achieve low cavity losses. In all of the embodiments disclosed, it is preferred that the optical cavities are stable optical cavities. Stable optical cavities are described in *Lasers*, by A. G. Seigman (University Science Books, California 1986), incorporated herein by reference.

In FIG. 2, a single element cavity 20 is formed by two high-reflectivity coated surfaces 22 and 24 and a convex superpolished surface 26 on cavity medium 28. The reflective surfaces 22 and 24 are preferably orthogonal to one another and the cavity medium is preferably fused silica. A light source 29, described throughout as a laser, is positioned adjacent to reflective surface 22 and produces light indicated as 30. The laser is preferably a diode laser. In another preferred embodiment, the light source 29 is a pulsed, dye laser used with frequency scanning. A detector 34 is positioned adjacent to reflective surface 24. In one preferred embodiment, the detector 34 is a photomultiplier. The cavity medium 28 provides a total internal reflection with very high internal transmission for a light beam 30 at the convex superpolished surface 26.

Since the total internal reflection occurs at the convex surface 26 of the cavity medium 28, an evanescent wave 32 is produced which decays exponentially into the region external to the convex surface 26. Absorbing materials 33 placed within the decay length of the evanescent wave 32 can thereby be sensitively probed through the change in the decay time of a laser pulse injected into cavity 20. This decay time is detected by detector 34 which senses a very small portion of the injected light which escapes through reflective surface 24. Cavity losses for the configuration shown in FIG. 2 are minimized through the use of ultra-high transmission optical materials, ultra-high reflectivity coatings, superpolishing, and proper cavity design.

In a preferred embodiment, the detector 34 senses the intensity of the light passing through reflective surface 24 and feeds the resultant signal to a digitizing means (not shown). In one preferred embodiment, the digitizing means is a digital oscilloscope. The decay time $\tau(\omega)$ of the digitized signal is approximated by:

$$\tau(\omega) = t_r / (2(1-R) + \zeta_{bulk} \zeta_{surf} + \zeta_{abs})$$

where $t_r$ is the round-trip time in the cavity, R is the reflectivity of the coated surfaces 22, 24 and 26, $\zeta_{bulk}$ is the bulk attenuation by the cavity medium 28, $\zeta_{surf}$ is the surface scattering loss at the total internal reflecting surface 26 and $\zeta_{abs}$ is the optical absorption by the absorbing material 33.

All of the loss terms in the decay time formula are known and are constant for a given cavity design except the optical absorption of the absorbing material $\zeta_{abs}$. Therefore, a measurement of the actual photon decay time allows one to obtain the unknown quantity $\zeta_{abs}$.

The use of a single optical element for the optical cavity 20 results in a more rugged cavity as compared to other, multi-element cavities. In addition, the single element cavity 20 allows for remotely positioning the cavity 20 from the light source 29 and the detector 32 without the burden of aligning plural elements. The light source and detector may be optically coupled to the optical cavity with fiber optic materials (not shown).

In an alternative preferred embodiment, a picosecond or femtosecond pulsed laser with continuum generation is used as the light source and frequency analysis of the output signal is performed either by interferometry or dispersion methods.

In general, it is important to note that although the cavity design is quite simple, the surface quality required to produce a sufficiently high Q-factor necessitates the use of state-of-the-art polishing techniques, which can produce surfaces with <0.1 nm RMS surface roughness. Furthermore, these cavities form stable optical resonators, so that an injected light pulse will retrace its path in the cavity a large number of times. The beam waist associated with the stable mode of the cavity is located in the vicinity of the totally reflecting surface to optimize spatial resolution. In the embodiments of FIGS. 1 and 2, the sample is probed by the light pulse a number of times N, equal to the ratio of the decay time to one-half the round trip time. This value will typically be on the order of 1,000.

Anticipated commercial applications for the invention include:
1. Biosensor applications
2. Catalysis
3. Corrosion
4. Adhesion
5. Trace analysis for semiconductor processes
6. Chromatography detector
7. Process measurements
8. Optical constant determinations
9. Hostile environments
10. Trace analysis in general
11. Research tool for surface science research Although the present invention has been described to specific exemplary embodiments thereof it will be understood by those skilled in the art that variations in modifications can be effected in these exemplary embodiments without departing from the scope and spirit of the invention.

I claim:

1. An intra-cavity total reflection apparatus for high sensitivity measurement of the optical absorption of a test material, said apparatus comprising:

injecting means for producing light for a predetermined length of time;

an optical cavity, comprising first, second and third reflecting surfaces integrally formed on a cavity medium, for receiving said light produced by said injecting means and for providing total internal reflection of said light within said cavity so as to generate an evanescent wave at said third reflecting surface which decays within a decay length outside of said cavity beyond said third reflecting surface, the test material being disposed outside of said cavity within said decay length, and said injected light oscillating between said first and second reflecting surfaces such that a portion of said injected light escapes from said cavity; and measuring means disposed adjacent one of said first and said second reflecting surfaces for monitoring said portion of said injected light that escapes from said cavity to determine the amount of decay time said light takes to decay within said cavity and the optical absorption of said test material.

2. An apparatus as claimed in claim 1, wherein said measuring means comprises a photomultiplier.

3. An apparatus as claimed in claim 1, wherein said first and said second reflecting surfaces are orthogonal to one another.

4. An apparatus as claimed in claim 1, wherein said cavity medium is formed of fused silica.

5. An apparatus as claimed in claim 1, wherein said injecting means an said measuring means are optically coupled to said optical cavity with fiber-optic waveguides.

6. An apparatus as claimed in claim 1, wherein said third reflecting surface is a convex surface.

7. An apparatus as claimed in claim 1, wherein said injecting means comprises a laser.

8. An apparatus as claimed in claim 7 wherein said laser comprises one of a pulsed dye laser, a picosecond pulsed laser, a femtosecond pulsed laser and a continuous wave laser.

9. An apparatus as claimed in claim 7 wherein said laser comprises a diode laser.

* * * * *